United States Patent [19]
Kelman

[11] Patent Number: 4,781,719
[45] Date of Patent: Nov. 1, 1988

[54] METHOD OF INSERTING AN INTRAOCULAR LENS INTO AN EYE

[76] Inventor: Charles D. Kelman, 269 Grand Central Pkwy., Floral Park, N.Y. 11005

[21] Appl. No.: 78,563

[22] Filed: Jul. 28, 1987

[51] Int. Cl.$^4$ .................................................. A61F 2/16
[52] U.S. Cl. .................... 623/6; 128/303 R; 206/5.1
[58] Field of Search ............ 623/6; 128/303 R; 206/5.1

[56] References Cited

U.S. PATENT DOCUMENTS

| | | | |
|---|---|---|---|
| 4,534,069 | 8/1985 | Kelman | 623/6 |
| 4,573,998 | 3/1986 | Mazzocco | 623/6 |
| 4,638,056 | 1/1987 | Callahan et al. | 623/6 X |
| 4,681,102 | 7/1987 | Bartell | 128/303 R |
| 4,715,373 | 12/1987 | Mazzocco et al. | 623/6 X |

*Primary Examiner*—Ronald L. Frinks
*Attorney, Agent, or Firm*—Henry Sternberg; Bert J. Lewen

[57] ABSTRACT

Method of inserting an intraocular lens, having an optic and haptics of flexible material, through an incision into an eye, including preliminarily compressing the lens into a generally cylindrical shape, e.g. in a tubular sleeve, immersing the compressed lens in an eye compatible liquid, e.g. water, freezing the liquid in situ to form a generally cylindrical frozen plug, and inserting the frozen plug, containing the compressed lens therein, through the incision into the interior of the eye, e.g. by positioning such sleeve external to the eye at the incision and pressing the frozen plug by a plunger in the direction of the eye so as to force the plug out of the sleeve and in unconfined condition through the incision, such that the inserted plug will thaw in the eye interior and release the lens to its original, undeformed state, whereupon the original state lens may be seated in place in the eye.

19 Claims, 2 Drawing Sheets

U.S. Patent  Nov. 1, 1988  Sheet 1 of 2  4,781,719
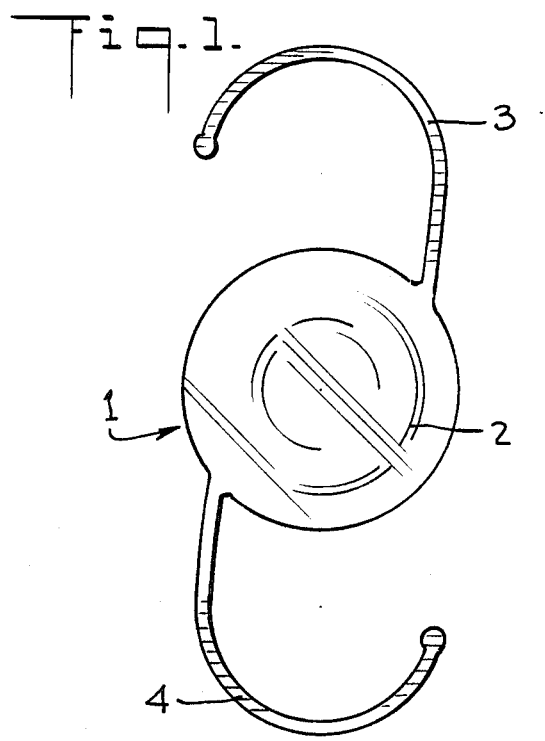
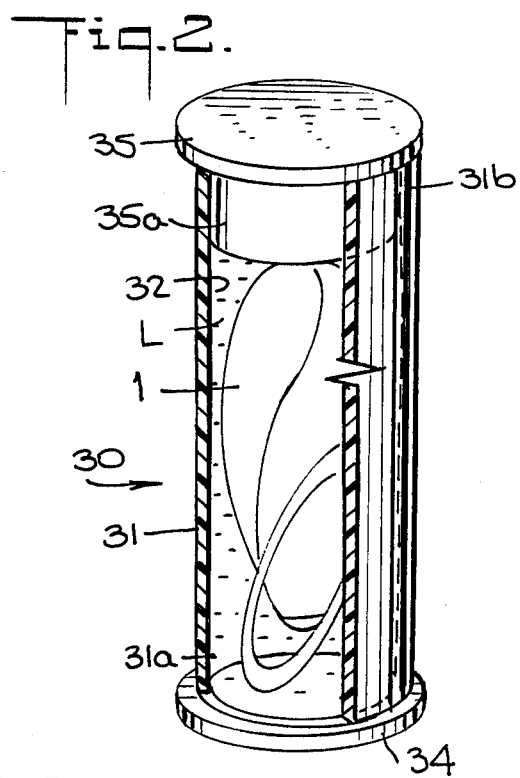
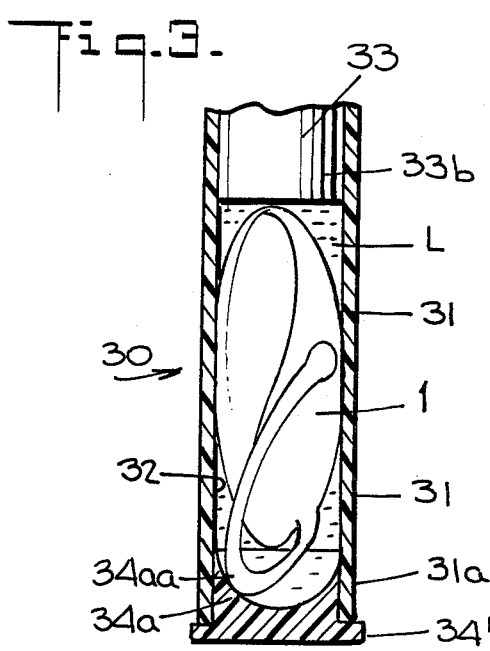
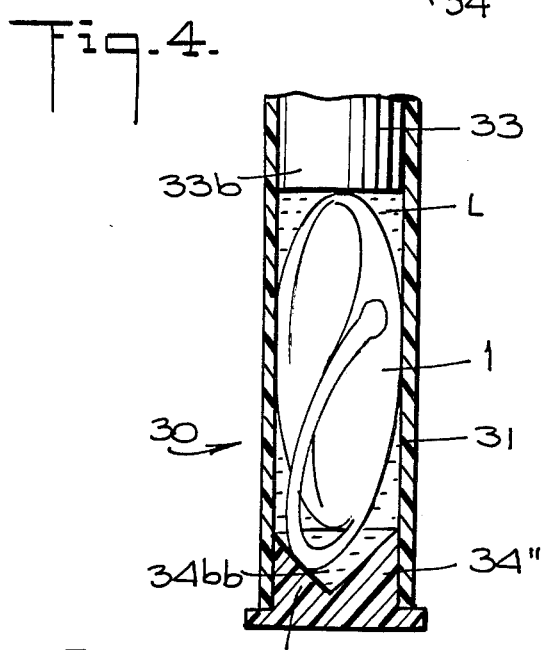
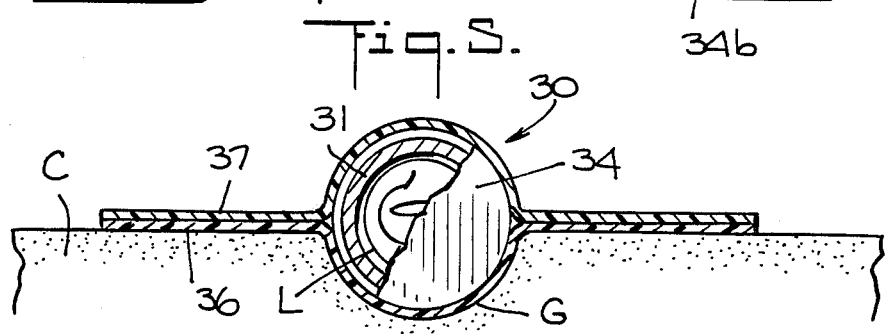

METHOD OF INSERTING AN INTRAOCULAR LENS INTO AN EYE

FIELD AND BACKGROUND OF THE INVENTION

The present invention relates to a method of inserting an artificial intraocular lens into an eye, and more particularly to a method of deforming such lens and inserting it in deformed state into the eye through a corneal incision of minimal size.

In eye surgery for treatment of conditions such as natural eye lens cataracts, a common procedure is to remove the cataracted lens through an incision in the wall of the cornea of the eyeball, and replace it by an artificial intraocular lens. Intraocular lenses are usually made flexible, foldable, etc., to permit size reduction thereof for facilitating their insertion through the cornea, with the highly advantageous result that an incision of absolute minimum size will suffice.

Even though their lens bodies or optics may be curlable, foldable or otherwise deformable to reduce their overall girth, such intraocular lenses, for example silicone lenses, often have haptics extending from the periphery of their optics, i.e. normally expanded resilient appendages connected to the central lens body or optic, to aid lens seating in the eye. Preferably, these flexible lenses must somehow be maintained in curled, folded or similar reduced girth condition, with their haptics in contracted state, during insertion into the eye in order to fit without difficulty through a minimum size incision.

U.S. Pat. No. 4,573,998 to Mazzocco (Mazzocco '998), and U.S. Pat. No. 4,534,069 to Kelman (Kelman '069), are among typical proposals which have been made to provide the intraocular lens in temporarily reduced girth condition for incision insertion purposes.

Mazzocco '998 contemplates curling the silicone or the like optic, together with the haptics, in the form of a lens compact in a sleeve type instrument, inserting the sleeve end physically through the eye incision, and forcing the compacted lens, with the aid of a plunger or the like, out of the sleeve end while the end projects into the eye through the incision. However, this approach requires that the incision must be large enough to permit insertion therethrough of not only the lens, but also the sleeve end.

It would, of course, be highly advantageous if only the compacted lens and not also a sleeve instrument needed to be inserted into the eye, since the incision could then be made of substantially reduced size, considering that the sleeve wall thickness adds to the lens girth at both diametric sides.

Kelman '069 provides one solution to this problem, by temporarily molding the lens, with the haptics in contracted state overlapping the central optic, in a layer of adhesive acting material which is non-toxic and otherwise compatible with as well as soluble in the eye fluid, and which connects the haptics in that contracted state to the optic during lens insertion into the eye through the incision, yet such solution does not involve physically grossly deforming the overall lens mass to reduce its girth.

SUMMARY OF THE INVENTION

It is among the objects and advantages of the present invention to overcome the drawbacks and deficiencies of the prior art, as regards eye surgery for removal of a natural eye lens and replacement thereof in the eye by an artificial intraocular lens, and to provide a method of inserting an intraocular lens of flexible, especially deformable, material through an incision into an eye, such as a lens having an optic and haptics, in a reduced girth form permitting use of a minimum size corneal incision, and which avoids physical insertion of any extraneous sleeve or other gross mechanical instrument into the incision for achieving the desired introduction of the intraocular lens.

It is among the additional objects and advantages of the present invention to provide a method of the foregoing type, which involves a minimum of steps and materials for preparing the intraocular lens to achieve the desired reduced girth form, and which enables the actual insertion of the lens to be effected in efficient and comparatively rapid manner, with minimum trauma to the patient.

It is among the further objects and advantages of the present invention to provide an insertion method of the stated type which is relatively safe in practice, and which utilizes inexpensive and readily available materials and implements for preparing the reduced girth form lens for such insertion.

According to the present invention, a method of inserting an intraocular lens, having an optic and haptics, of flexible material, through an incision into an eye is provided, which comprises compressing the lens into a generally cylindrical shape, immersing the compressed lens in an eye compatible liquid, freezing the liquid in situ to form a generally cylindrical frozen plug, and inserting the frozen plug, containing the compressed lens therein, through the incision into the interior of the eye.

Desirably, the lens is maintained sterile in the sleeve during the compressing, immersing and freezing steps. Once inserted, the plug is allowed to thaw in the interior of the eye for releasing the lens to its original, undeformed state, and the original state lens may then be seated in place.

The compressing of the lens favorably includes pressing the lens into the confining interior of a tubular sleeve, its immersing includes filling the resulting spaces, between the compacted lens and the sleeve interior surrounding the lens, with water or other non-toxic eye fluid compatible and soluble liquid capable of freezing, and the freezing includes withdrawing heat from the liquid in the sleeve so as to freeze such liquid and form the latter into a frozen plug having the lens in compressed immobile condition therein. The sleeve may be provided with a plunger at one end thereof, such that the inserting of the lens into the eye may be effected by positioning the sleeve external to the eye at the incision and pressing the plunger in the direction of the eye so as to force the frozen plug out of the sleeve and in unconfined condition through the incision.

The withdrawing of heat from the liquid may be effected by subjecting the sleeve and its liquid contents to a coolant, such as dry ice, e.g. by positioning the sleeve and its liquid contents in a groove in such dry ice.

BRIEF DESCRIPTION OF THE DRAWINGS

Other and further objects and advantages of the present invention will become apparent from the within specification and accompanying drawings, in which:

FIG. 1 is a plan view of one embodiment of an intraocular lens, having an optic and haptics, of flexible material, usable in accordance with the method of the present invention;

FIG. 2 is a perspective view of the lens of FIG. 1 in compressed condition, immersed in a liquid in the interior of a sleeve, prior to freezing the unit;

FIGS. 3 and 4 are sectional side views of corresponding modified portions of the unit of FIG. 2, showing the disposition in the sleeve interior of the liquid immersed lens in relation to the inserted end of a plunger in the sleeve interior at the compressed lens rear end portion, and also, respectively, in FIG. 3 in relation to the concave rounded inner projection, and in FIG. 4 in relation to the concave pointed or conical inner projection, of so modified end caps at the compressed lens front end portion, of the unit;

FIG. 5 is a side view of the unit of FIG. 2, covered by sterile sheeting, and positioned in a groove of a block of dry ice used for freezing the immersing liquid to form a corresponding reduced girth frozen plug containing the lens;

DESCRIPTION OF THE PREFERRED EMBODIMENTS

Figure 7:
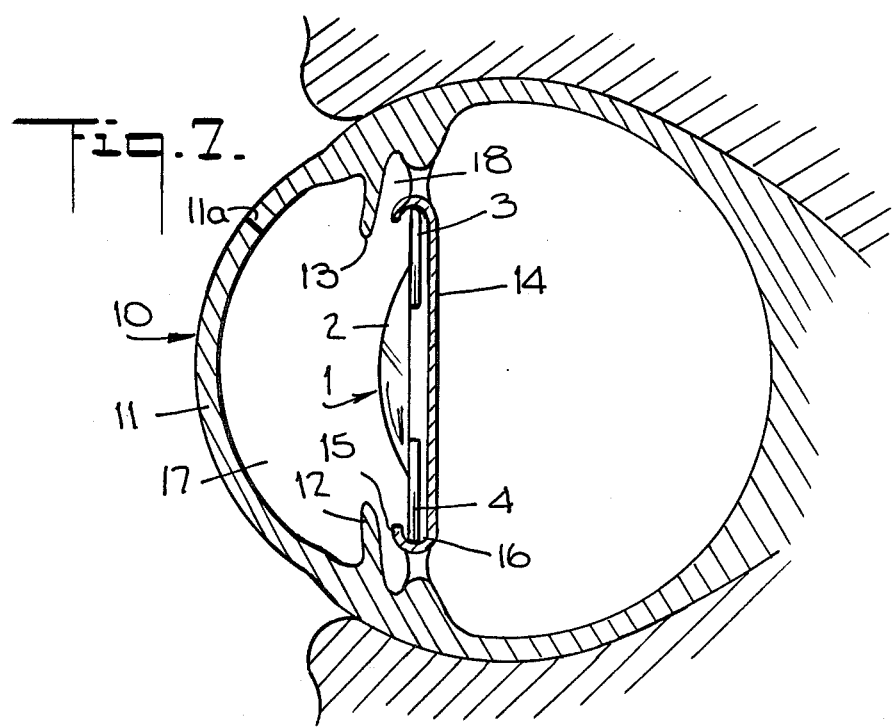
FIG. 7 is a view similar to FIG. 6, showing the lens in its original, undeformed state, i.e. after the plug has thawed, and seated in place with the haptics in extended supporting disposition.

Referring to the drawings, and initially to FIGS. 1 and 7, an embodiment of a flexible, and preferably readily temporarily deformable, artificial intraocular lens 1 of conventional type is shown, which is usable in accordance with the method of the present invention for insertion into the interior of an eye through a corneal incision of minimized size for replacing the natural lens, such as a cataracted lens.

Lens 1 has a light focusing lens body or optic 2 and is desirably provided with a symmetrical pair of position fixation means or haptics 3,4 or the like, i.e. oppositely disposed outwardly flaring resilient eye seating appendages (FIG. 1). Haptics 3,4 or the like are used for embracing the adjacent portions of the eye interior for seating lens 1 in the usual manner in the anterior chamber, or in the posterior chamber, or as for example indicated in FIG. 7, in the posterior capsule, once the intraocular lens has been inserted through the incision in the cornea and positioned for such seating, as described more fully in said U.S. Pat. No. 4,534,069 to Kelman, the disclosure of which is incorporated herein by reference.

As to the arrangement shown in FIG. 7, the here pertinent parts of the human eyeball 10 include the cornea 11, iris 12 with its central opening or pupil 13, posterior capsule 14 and in this instance the remainder of anterior capsule 15 after extracapsulary removal of a cataracted natural lens, such that posterior capsule 14 defines a cul-de-sac 16 at its peripheral margins which is formed between posterior and anterior capsules 14,15. The eye interior contains an aqueous humor zone between cornea 11 and posterior capsule 14, which is divided by iris 12 into an anterior chamber 17 and a posterior chamber 18.

It is clear from FIG. 7 that haptics 3,4 or the like are adapted to seat in the cul-de-sac 16 formed between posterior and anterior capsules 14,15 to maintain lens 1 in proper position for optic 2 to perform its light focusing function. Alternatively, haptics 3,4 or the like may be adapted to seat in anterior chamber 17, in the ciliary sulcus between iris 12 and anterior capsule 15, or in any other suitable location in the eye in a manner well known to those skilled in the art.

In this regard, optic 2 of lens 1 may have a diameter of about 6 mm and a thickness of about 2.5 mm, and each of the haptics 3,4 or the like may have a thickness of about 0.2 mm and a width, i.e. in the plane of the paper of FIG. 1, of about 1.2 mm. Haptics 3,4 may be of any suitable shape well known in the art and may have a maximum composite expanded length dimension in normal, non-contracted condition of about 13 mm from the outer edge or crest portion of one haptic to the diametrically opposite outer edge or crest portion of the other haptic in the elongate direction as shown in FIG. 1.

Lens 1 may be formed of any suitable light focusing optic serving material, which is sufficiently flexible to enable the desired at least two haptics or like appendages thereof to perform in the contemplated lens positioning manner, and which is compatible with the environment in the interior of the eyeball, such as a non-toxic plastic, for example silicone.

More particularly, for the purposes of the present invention, the material of lens 1 must be sufficiently flexible to permit its mass to be grossly deformed, e.g. with appropriate curling, folding, crinkling and the like of such mass, spatially inwardly in a direction to reduce its apparent composite girth, and preferably also to be deformed, spatially longitudinally in the direction of its spatial dimension taken as its length.

The contemplated lens material is normally sufficiently flexible to have a temporary resilient memory, such that even if the lens mass is deformed to provide the same in compressed condition for reducing its girth, and maintained in such compressed condition for an extended period of time, for example at freezing temperatures, it will thereafter still return readily to its original expanded state. Nevertheless, the period of time such mass is kept deformed under such compressed conditions, e.g. at freezing temperatures, should not be more than several hours to insure that there will be no permanent loss of such resilient memory.

As may be seen from FIGS. 2-6, according to the method of the present invention, lens 1 is preliminarily prepared under aseptic conditions as a generally cylindrical frozen plug P for insertion by the surgeon through corneal incision 11a, by the steps of compressing lens 1 into a generally cylindrical shape, immersing compressed lens 1 in a non-toxic, eye fluid compatible and soluble liquid L which is capable of freezing, and freezing liquid L in situ.

This may be favorably accomplished in sterile unit 30 of FIG. 2, by use of a simple tubular sleeve 31, e.g. of suitable plastic, such as Teflon, or the like, having a hollow interior or bore 32 of appropriate generally cylindrical internal shape, into which the so deformable flexible mass of lens 1 is pressed via either sleeve exit end 31a or sleeve plunger receiving end 31b. Preferably, lens 1 is deformed, for example by a plierlike instrument similar to the forceps type grasping and compressing instrument shown by Mazzocco '998, or the like, and is then inserted, in such deformed condition, e.g. in curled, folded and/or crinkled condition, into sleeve plunger receiving end 31b. The coacting plunger 33, preferably also of Teflon, or the like, of conforming size and shape to bore 32, which is arranged for sliding relative movement with respect to bore 32 in sealing relation thereto in the manner of a piston in a cylinder, is used to ram lens 1 along the confining interior of bore 32, e.g. until its forwardmost so compressed mass portion is substantially flush with the end plane of exit end 31a, for example, which may be achieved by temporarily placing an end plate or cap 34 of conforming internal flat planar or plate shape on sleeve 31 to close exit end 31a.

Thereafter, unit 30 may be raised to upright vertical position, with the exterior rear end 33a of plunger 33 extending downwardly from the now lower sleeve plunger receiving end 31b, and with the inserted forward end 33b of plunger 33 in sliding sealing relation with respect to surrounding bore 32 and extending upwardly toward the now upper sleeve exit end 31a, and a sterile, non-toxic, eye fluid compatible and soluble liquid L capable of freezing, such as distilled water, then poured into bore 32 through the now upper exit end 31a (after temporary removal of end cap 34) so as to immerse lens 1 therein, with liquid L filling the resulting intervening and interconnected spaces between compacted lens 1 and the surrounding interior of bore 32.

Figure 6:
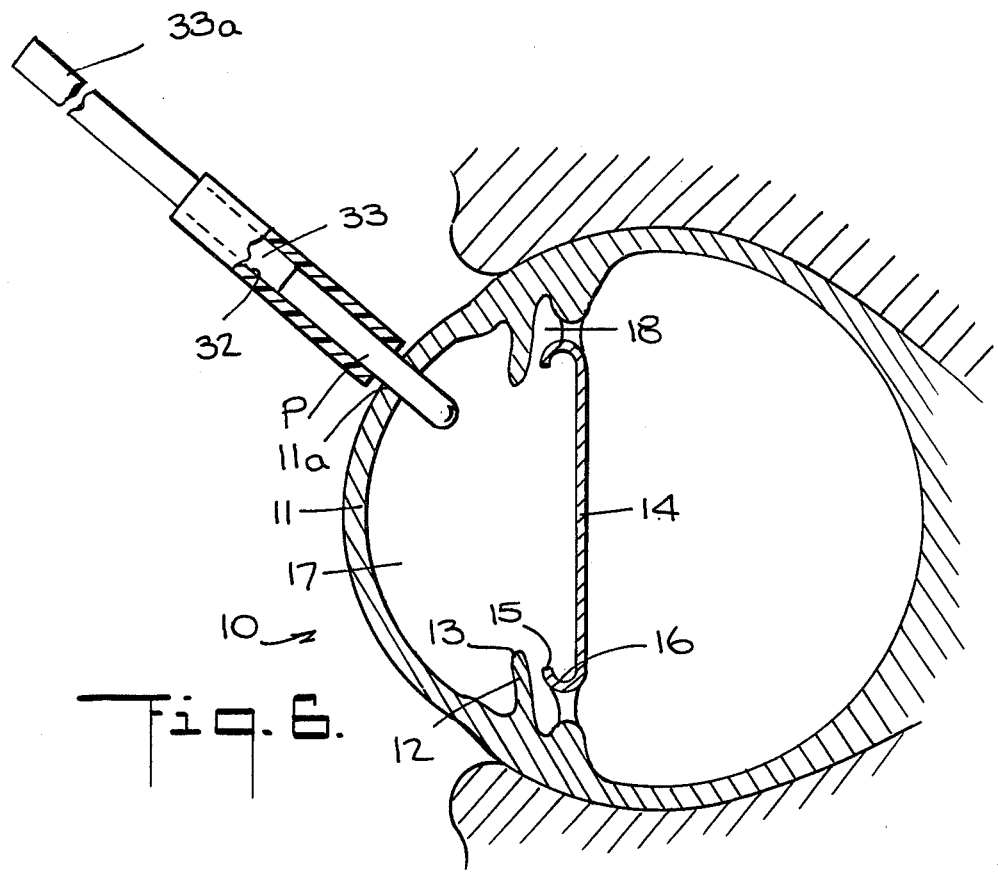
FIG. 6 is a schematic view showing the manner of inserting one form of the frozen plug in unconfined condition through the corneal incision into the interior of the eye.

Unit 30, preferably with plunger 33 and end cap 34 in place, may then be positioned in operative heat exchange relation with a coolant for withdrawing heat from liquid L in sleeve 31 so as to freeze liquid L in situ in enveloping conforming disposition around the curls, folds and/or crinkles of the compressed and deformed lens 1, and thereby form the latter into a self contained frozen plug P having the lens in compressed immobile condition therein (FIG. 6).

For example, vertical unit 30 with upper exit end 31a open may be merely placed in upright condition in operative contact with a block of dry ice C as coolant. Alternatively, after filling bore 32 with liquid L to refusal, end cap 34 may be again placed over the open exit end 31a (FIG. 2), and unit 30 merely laid in a horizontal groove or bore G in a block of dry ice C, as shown in FIG. 5, or further alternatively, plunger 33 may be replaced at plunger receiving end 31b by end cap 35 having an internal projection 35a (FIG. 2), for positional adjustment of lens 1 within bore 32 in like manner to the functioning of the inserted forward end 33b of plunger 33, whereby to seal lens 1 and liquid L within bore 32 by both caps 34 and 35 (FIG. 2).

Advantageously, in accordance with a feature of the present invention, plunger 33 may simply be maintained in sleeve end 31b during the freezing step to act as the seal, and the freezing can then be performed with unit 30, containing plunger 33 and end cap 34, in horizontal or any other disposition.

According to the respective alternative modification embodiments of FIGS. 3 and 4, end cap 34 may be formed with an internal projection having a rounded or pointed cavity opening toward the interior of bore 32. Specifically, where modified end cap 34' is formed with an internal projection 34a having a rounded, e.g. hemispherical, cavity 34aa (FIG. 3), the resulting frozen plug P (FIG. 6) will have an insertion end Pi provided with a conforming rounded tip, and alternatively where modified end cap 34" is formed with an internal projection 34b having a pointed, e.g. conical, cavity 34bb (FIG. 4), such plug P will have an insertion end Pi provided with a conforming pointed tip. These modified insertion end or bullet shape plugs will facilitate insertion of the given plug through the corneal incision.

In any case, thin sterile sheeting 36,37 of rubber or other suitable material, or a sealable envelope of such material, is favorably used to enclose and/or isolate the otherwise exposed surfaces of unit 30 from the environment, to preserve the sterile condition of unit 30, and especially of lens 1 and liquid L (FIG. 5). Naturally, all steps and procedures as well as materials and objects contemplated for achieving formation of frozen plug P are utilized in sterile condition while adhering throughout to sterile technique.

When the surgical procedure is to take place, unit 30 is retrieved. Of course, unit 30 should not remain in frozen condition more than a few hours before use, so as to avoid any possible permanent loss of memory of the resilient lens mass as might otherwise be caused by keeping the same for an overextended period under such compressed and distorted conditions. Therefore, the freezing of unit 30 should be undertaken at most only a few hours before the surgeon conducts the actual insertion procedure.

If unit 30 was subjected to the coolant in vertical position with plunger 33 in place and without caps 34 (or 34' or 34") and 35, it may be used as is. On the other hand, if unit 30 was subjected to the coolant in horizontal position with both plunger 33 and cap 34 (or 34' or 34") in place, or with cap 34 (or 34' or 34') in place and plunger 33 temporarily replaced by cap 35, any such caps are removed and if absent plunger 33 is again inserted.

Then, as shown in FIG. 6, exit end 31a of sleeve 31 is positioned and held by the surgeon adjacent the exterior of corneal incision 11a, and plunger 33 is simply pressed in the direction of eyeball 10 so as to force frozen plug P out of sleeve 31 and in unconfined condition via its insertion end Pi, preferably modified with a rounded or pointed tip per use during the freezing step of end cap 34' or 34" on exit end 31a of unit 30 (FIG. 3 or FIG. 4), through incision 11a and into anterior chamber 17 independently of sleeve 31 or any other extraneous physical instrument occupying the incision. Plug P immediately begins to thaw within anterior chamber 17 whose aqueous humor fluid is at body temperature.

As soon as liquid L in plug P has sufficiently melted, which takes place relatively rapidly considering the small mass of frozen plug P compared to the large mass of body temperature aqueous humor fluid in anterior chamber 17, lens 1 is released to its original, expanded and undeformed state (FIG. 1), and may be readily seated by the surgeon in normal manner in the eye as, for example, shown in FIG. 7.

Thus, according to the present invention, the artificial intraocular lens is preliminarily compacted into generally cylindrical form, placed in an enveloping liquid environment, and frozen in situ. The frozen plug formed from the liquid immersed compacted lens, such as an ice plug, represents a conveniently shaped, small size girth, temporary insert element, preferably having a rounded or pointed insertion end, which contains the lens in generally cylindrically, compacted immobile condition therein, and which is capable upon thawing of returning to its original expanded size.

The plug is preferably formed in a cylindrical sleeve having an open exit end and opposed plunger receiving end for accommodating a coacting plunger in its interior bore in the manner of a piston-cylinder arrangement. In particular, the sleeve is preferably formed of Teflon or like type commercially available plastic material, which desirably possesses enhanced lubricity even at freezing temperatures, as well as sufficient structural integrity to withstand mechanical stresses generated during lens insertion into its bore, liquid expansion during freezing as in the case of water, and pressing expulsion, under the urging force of the plunger inserted in the sleeve plunger receiving end, of the frozen plug from the bore at the open exit end during surgical insertion of the plug through the corneal incision.

For similar reasons, the plunger is also preferably formed of such Teflon or like type plastic material.

Understandably, the interior bore of the sleeve is of such size that the lens of silicone, or the like plastic material, including both the optic and haptic components, fits tightly therein, in grossly deformed or distorted curled-up, folded and/or crinkled generally cylindrical apparent shape, and is able to slide therealong with minimum friction, in a manner analogous to the tight sealing and sliding relation between the counterpart generally cylindrical shape plunger and sleeve bore.

In this regard, the term "cylindrical" is used herein to comprehend not only a true right cylindrical geometric shape but also analogous elongate shapes, including those of out-of-round, oblate, and polygonal cross sectional profile, produced from sleeves as molds for the plug which have correspondingly shaped internal bores, as these shapes are likewise appropriate for enabling the reduced girth apparent profile plug to be inserted readily through the intended minimum size corneal incision.

Furthermore, such "cylindrical" shapes are intended to comprehend as well those providing modified insertion ends for the resulting plugs for facilitating insertion thereof through the corneal incision safely and with minimum trauma or discomfort to the patient, and especially bullet shaped plugs having a rounded or pointed tip at their insertion end for ease of such insertion through the incision.

Besides water, the liquid used to immerse the lens in the sleeve may also be any other non-toxic, eye fluid compatible and eye fluid soluble liquid capable of freezing, such as Healon, since the purpose of the liquid poured into the sleeve bore is to fill up the interconnecting, especially peripheral, spaces remaining between the relatively tightly curled, folded and/or crinkled lens and the inner walls of the sleeve, sufficiently that upon placing the unit in a heat withdrawal or cooling arrangement such as a freezing apparatus, the liquid will freeze to form a structure confining the compacted lens, and keeping the latter in immobile reduced girth condition.

As will be appreciated, the cooling arrangement may take any conventional form. While the unit of the sleeve with the lens and liquid therein may be simply placed in heat exchange cooling relation with a block of dry ice, e.g. in a bore or groove therein, as aforesaid, alternatively a thermo-electric apparatus, for example, may be used for quickly reducing the temperature of the liquid and lens. As a further alternative, the unit may be placed in a container into which a coolant, such as liquid nitrogen from a tank supply thereof, or carbon dioxide from a $CO_2$ pressure cylinder, or the like, may be directed so as to flush the sleeve therewith and freeze rapidly the contents thereof.

In all such instances, of course, precautions should be taken to maintain the lens, its surrounding liquid, and the sleeve, in sterile condition, by appropriate aseptic procedures.

As to the actual insertion of the frozen plug into the eye, since the sleeve need not enter the corneal incision, its girth dimensions may be of any appropriate non-critical size, and since the lens itself is in reduced girth form, such incision can be of greatly reduced size, as compared to that required in the case of conventional lens insertion procedures. Such insures that the procedure will be able to be carried out as safely as possible and with minimum trauma to the patient, especially where the plug is of said bullet shape.

In fact, the frozen plug need have a diameter no greater than the diameter of the cylindrically compacted lens, since even if edge portions of the lens are exposed at the periphery of the plug, the frozen liquid which provides temporary structural integrity to the plug will encapsulate and immobilize sufficient portions of the mass of the lens to maintain the latter in compacted condition until passage of the plug through the incision and into the eye interior. Hence, the sleeve bore diameter can be selected to achieve the smallest size for the plug girth consistent with the deformation characteristics of the lens in question.

It should be noted that the method of the present invention can be carried out not only with a lens of the type shown in FIG. 1, but also with any other appropriate type lens of flexible, and preferably deformable, non-toxic and eye fluid compatible material such as a plastic material, including in particular silicone, and the like, with any associated haptic or the like position fixation members being of the same type material, or even a comparatively more flexible material such as polypropylene.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Method of inserting an intraocular lens, having an optic and haptics of flexible material, through an incision into an eye, which comprises compressing the lens into a generally cylindrical shape, immersing the compressed lens in an eye compatible liquid, freezing the liquid in situ to form a generally cylindrical frozen plug, and inserting the frozen plug, containing the compressed lens therein, through the incision into the interior of the eye.

2. Method of claim 1 including allowing the inserted plug to thaw in the interior of the eye for releasing the lens to its original, undeformed state, and seating the original state lens in the eye.

3. Method of claim 1 wherein the compressing of the lens includes pressing the lens into the confining interior of a tubular sleeve.

4. Method of claim 3 wherein the immersing of the lens includes filling the resulting spaces, between the compacted lens and the sleeve interior surrounding the lens, with water or other liquid capable of freezing.

5. Method of claim 4 wherein the freezing includes withdrawing heat from the liquid in the sleeve so as to freeze such liquid and to form the latter into a frozen plug having the lens in compressed immobile condition therein.

6. Method of claim 5 wherein the sleeve is provided with a plunger at one end thereof, and the inserting of the lens into the eye includes positioning the sleeve external to the eye at the incision and pressing the plunger in the direction of the eye so as to force the frozen plug out of the sleeve and in unconfined condition through the incision.

7. Method of claim 5 wherein the withdrawing of heat from the liquid includes subjecting the sleeve and its liquid contents to a coolant.

8. Method of claim 7 wherein the coolant is dry ice, and the withdrawing of heat includes positioning the sleeve and its liquid contents in a groove in such dry ice.

9. Method of claim 8 wherein the lens is maintained sterile in the sleeve during the compressing, immersing and freezing steps.

10. Method of claim 1 wherein the liquid is frozen into a generally cylindrical plug having an insertion end provided with a pointed tip.

11. Method of claim 1 wherein the liquid is frozen into a generally cylindrical plug having an insertion end provided with a rounded tip.

12. Method of inserting an intraocular lens of flexible, deformable material through an incision of minimal size into an eye, which comprises freezing an eye compatible liquid in enveloping conforming disposition around the lens under sterile conditions, while maintaining the lens in compressed generally cylindrical deformed shape, to form a generally cylindrical self contained sterile frozen plug, and inserting the frozen plug in unconfined condition through the incision into the eye.

13. Method of claim 12 including allowing the inserted plug to thaw in the interior of the eye for releasing the lens to its original, undeformed state, and seating the original state lens in the eye.

14. Method of claim 12 wherein the lens is maintained in compressed shape immersed in the liquid in the generally cylindrical interior of a tubular sleeve during the freezing, the sleeve has an exit end, and the plug is inserted into the eye by positioning the exit end adjacent the exterior of the incision and forcing the plug outwardly of the exit end and in unconfined condition into and through the incision.

15. Method of claim 14 wherein the liquid is frozen by positioning the sleeve and its contents under sterile conditions in operative heat exchange relation with a coolant.

16. Method of claim 12 wherein the liquid is sterile water.

17. Method of claim 12 wherein the lens includes an optic and haptics of flexible, deformable material.

18. Method of claim 12 wherein the liquid is frozen into a generally cylindrical plug having an insertion end provided with a pointed tip.

19. Method of claim 12 wherein the liquid is frozen into a generally cylindrical plug having an insertion end provided with a rounded tip.

* * * * *